(12) United States Patent
Robbins et al.

(10) Patent No.: US 7,541,475 B2
(45) Date of Patent: Jun. 2, 2009

(54) SUBSTITUTED THIAZOLES

(75) Inventors: Timothy A. Robbins, Gurnee, IL (US); Helen Zhu, South Bend, IN (US); Jun Shao, Mason, OH (US)

(73) Assignee: Abbott Laboratories, Abbott Park, IL (US)

( * ) Notice: Subject to any disclaimer, the term of this patent is extended or adjusted under 35 U.S.C. 154(b) by 771 days.

(21) Appl. No.: 10/903,553

(22) Filed: Jul. 30, 2004

(65) Prior Publication Data
US 2005/0075503 A1  Apr. 7, 2005

Related U.S. Application Data

(60) Provisional application No. 60/491,089, filed on Jul. 30, 2003.

(51) Int. Cl.
*C07D 277/04* (2006.01)
(52) U.S. Cl. .................................... 548/201; 564/74
(58) Field of Classification Search ................ 548/201; 564/74
See application file for complete search history.

(56) References Cited

U.S. PATENT DOCUMENTS

| 3,518,279 | A | | 6/1970 | Miller et al. ............. 260/302 |
| 3,852,287 | A | | 12/1974 | Girgis .................... 260/247.1 |
| 5,880,288 | A | * | 3/1999 | Hollis et al. ............... 548/201 |

FOREIGN PATENT DOCUMENTS

| EP | 0 097 323 | 1/1984 |
| EP | 0 480 281 | 4/1992 |
| JP | 2002-53567 | 2/2002 |
| WO | 01/40207 | 6/2001 |

OTHER PUBLICATIONS

Abstract, Istanbullu et al. Hacettepe Universitesi Exzacilik Fakultesi Dergisi 6(1):21-8 (1986).
Abstract, Reissert; Grube: Chem. Ber. 42:3712 (1909).
Abstract: JP11060552.
Csavassy et al., "Synthese und Umsetzung von 2-Aryl-5-diazoacetyl-4-methyl-thiazolen," Liebigs Ann. Chem. 8:1195-1205 (1974).
Hasegawa, "A Facile One-Pot Synthesis of 4-Alkoxy-1,3-Benzenedicarbonitrile," Heterocycles 47(2):857-864 (1998).
Rapaport et al., "Chemiluminescence of Linear Hydrazides," Journal of the American Chemical Society 94(9):31523-3159 (1972).
Cassar et al., "Synthesis of thioamides from nitriles and hydrogen sulphide in the presence of phase-transfer catalysts," Communications 917-919 (1978).
Chabrier et al., "The thiamides," Bull Soc. Chim. Fr. 16[D] 272-296 (1949).
Hurd et al., "The preparation and chmical properties of thionamides," Chem. Rev. 61:45 (1961).
Schoberl et al., "Asym. Synthesis by Grignard reaction," Methoden der Orgaaischen Chemie, 4(9):741 (1955).
Walter et al., "Syntheses of Thiocarboxamiedes," Angew. Chem. Int. Ed. Engl. 5:447-461 (1966).
Walter et al., "Newer methods of preparatory organic chemistry—IV Syntheses of thiocarboxylic acid amides," Angew. Chem. 78(10):517-532 (1966).
Walter et al., Chemistry of Amides 383-475 (1970).

* cited by examiner

*Primary Examiner*—Kamal A. Saeed
(74) *Attorney, Agent, or Firm*—Johanna M. Corbin

(57) ABSTRACT

This invention is directed to processes for making substituted thiazoles. The substituted thiazole, ethyl 2-(4-hydroxyphenyl)-4-methyl-1,3-thiazole-5-carboxylate, also known as TEI-6720, is useful for treatment of gout and hyperuricemia. This compound belongs to a class of substituted thiazoles that inhibit xanthine oxidase and thus block uric acid production.

20 Claims, No Drawings

SUBSTITUTED THIAZOLES

This application claims priority from U.S. Provisional Patent Application Ser. No. 60/491,089, filed Jul. 30, 2003.

FIELD OF THE INVENTION

This invention is directed to processes for making substituted thiazoles.

BACKGROUND OF THE INVENTION

The compound ethyl 2-(4-hydroxyphenyl)-4-methyl-1,3-thiazole-5-carboxylate, also known as TEI-6720, is useful for treatment of gout and hyperuricemia. This compound belongs to a class of substituted thiazoles that inhibit xanthine oxidase and thus block uric acid production.

The synthesis of TEI-6720 involves two steps. In the first step, an aryl nitrile is converted to a thioamide. In the second step the thioamide is converted to a thiazole. Because of the therapeutic usefulness of TEI-6720 there is sustained interest in improving the synthesis of substituted thiazoles in general and TEI-6720 in particular.

SUMMARY OF THE INVENTION

Accordingly, a first embodiment of this invention is directed to a process for making a compound having formula (I)

$$R^1—(C=S)—NH_2 \qquad (I),$$

in which $R^1$ is phenyl or phenyl substituted with one, two, three, or four substituents independently selected from the group consisting of $C_1$-$C_6$-alkyl, $C_2$-$C_6$-alkenyl, $C_2$-$C_6$-alkynyl, —OH, —F, —Cl, —Br, —I, and —NO$_2$, the process comprising the step of:
(a) reacting a compound having formula (II)

$$R^1—C≡N \qquad (II),$$

with $H_2S$ and a base.

Compounds having formula (I) are useful intermediates for preparing compounds having formula (IV)

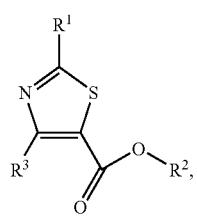

(IV)

in which $R^2$ is selected from the group consisting of hydrogen, $C_1$-$C_6$-alkyl, $C_2$-$C_6$-alkenyl, and $C_2$-$C_6$-alkynyl; and $R^3$ is selected from the group consisting of hydrogen, $C_1$-$C_6$-alkyl, $C_2$-$C_6$-alkenyl, and $C_2$-$C_6$-alkynyl.

Accordingly, a second embodiment of this invention is directed to a process for making the compound of formula (IV), the process comprising:
(b) reacting the compound having formula (I) and a compound having formula (V)

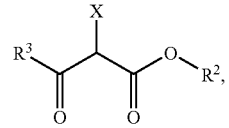

(V)

in which X is —Cl, —Br, —I, or —F.

DETAILED DESCRIPTION OF THE INVENTION

This invention discloses a novel process for isolating thioamides, key intermediates in the synthesis of TEI-6720. The isolation of the thioamide intermediate allows for cleaner synthesis of the thiazole and avoids the aqueous workup that was formerly required. Furthermore, the invention discloses a synthesis that eliminates the need for a catalyst, yet decreases processing time and increases the product yield. Overall, this invention allows large-scale synthesis and a commercially feasible process for making TEI-6720.

Definition of Terms

As used throughout this specification and the appended claims, the following terms have the following meanings:

All of the processes of the instant invention can be conducted as continuous processes. The term "continuous process," as used herein, represents steps conducted without isolation of the intermediates.

The term "alkenyl" as used herein, means a straight or branched chain hydrocarbon containing from 2 to 6 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, and 5-hexenyl.

The term "alkyl" as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkynyl" as used herein, means a straight or branched chain hydrocarbon group containing from 2 to 6 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The term "heteroaryl," as used herein, refers to an aromatic five- or six-membered ring wherein 1, 2, 3, or 4 heteroatoms are independently selected from N, O, or S. The five membered rings have two double bonds and the six membered rings have three double bonds. The heteroaryl groups are connected to the parent molecular moiety through a carbon or nitrogen atom. The term "heteroaryl" also includes bicyclic systems where a heteroaryl ring is fused to a phenyl group, a monocyclic cycloalkyl group, as defined herein, a heterocycle group, as defined herein, or an additional heteroaryl group; and tricyclic systems where a bicyclic system is fused to a phenyl group, a monocyclic cycloalkyl group, as defined herein, a heterocycle group, as defined herein, or an additional heteroaryl group. Representative examples of heteroaryl include, but are not limited to, benzothienyl, benzoxadiazolyl, cinnolinyl, dibenzofuranyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, tetrazolyl, thiadiazolyl, thiazolyl, thienopyridinyl, thienyl, triazolyl, and triazinyl.

The term "base," as used herein, represents a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; trialkylamines such as triethylamine, diisopropylamine, and diisopropylethylamine; heterocyclic amines such as imidazole, pyridine, pyridazine, pyrimidine, and pyrazine; bicyclic amines such as DBN and DBU; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "solvent," as used herein, refers to the dispersing medium of a solution. Examples of solvents include, $C_2$-$C_5$ alkylamides such as formaldehyde, N,N-dimethylformamide, N,N-dimethylacetamide, and the like; $C_4$-$C_6$ dialkoxyalkyls such as DME, 1,2-diethoxyethane, and the like; $C_1$-$C_4$ alcohols such as methanol, ethanol, propanol, iso-propanol, butanol, iso-butanol, sec-butanol, tert-butanol, and the like; $C_3$-$C_{10}$ ketones such as acetone, 2-butanone, 3-pentanone, 2-butanone, 2-pentanone, 2,5-heptanedione, and the like; $C_5$-$C_7$ hydrocarbons such as pentane, hexane, heptane, and the like; optionally substituted aromatic hydrocarbons such as benzene, toluene, 1,4-dichlorobenzene, nitrobenzene, and the like; ethers such as diethyl ether, diisopropyl ether, and the like; esters such as ethyl acetate isopropyl acetate, and the like; and water.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

Percentages such as % yield were obtained by HPLC analyses of starting materials and products. Values were calculated from the peak area.

Abbreviations

HPLC for high pressure liquid chromatography;

Synthetic Methods

The methods of this invention will be better understood in connection with the following synthetic scheme. It will be readily apparent to one of ordinary skill in the art that the compounds of this invention can be prepared by substitution of the appropriate reactants and agents in the synthesis shown below. The examples are provided to illustrate the embodiments and are no way intended to limit the scope of the invention.

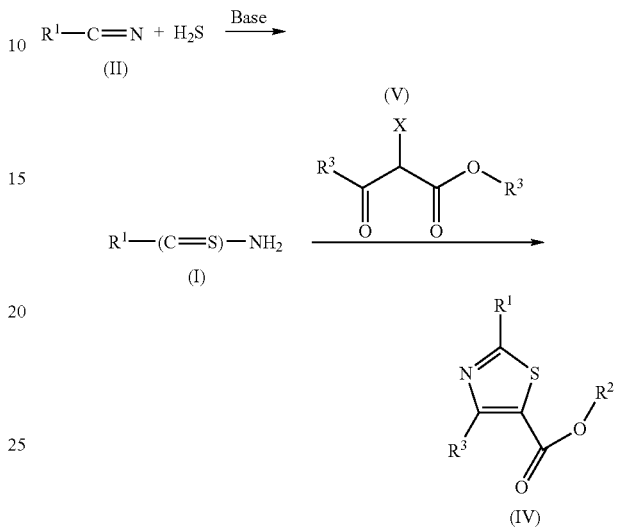

Scheme 1

In Scheme 1, conversion of compounds of formula (II) to compounds of formula (I) can be achieved by reaction of the former with $H_2S$ and a base in a solvent. In a preferred embodiment the base is a compound having formula (III)

$(M)^+(YH)^-$                                                             (III), in which M is sodium, potassium, lithium, or ammonium and Y is oxygen or sulfur. The reaction generally proceeds under a pressure of at least 10 psi and at a temperature of about 0° C. to about 150° C. for about 15 minutes to several days depending on the temperature and nature of the reactants. In a preferred embodiment this conversion is achieved at a pressure of 60 psi, a temperature of 70° C., and in a solvent of water.

Conversion of compounds of formula (I) to compounds of formula (IV) can be achieved by reacting compounds of formula (I) with compounds of formula (V) in a solvent. The reaction generally proceeds at a temperature of about 0° C. to about 150° C. for about 15 minutes to several days depending on the temperature and nature of the reactants. In a preferred embodiment this conversion is achieved at a temperature of 80° C. and in a solvent of ethanol.

In one embodiment of this invention, 4-hydroxybenzene carbothioamide (a compound of formula (I)) is prepared by reacting 4-hydroxybenzonitrile (a compound of formula (II)), $H_2S$, and sodium hydrogen sulfide (a base and compound of formula (III)) under a pressure of at least 10 psi at a temperature of about 0° C. to about 150° C. in a solvent. In a preferred embodiment of this invention, the pressure is 60 psi, the temperature is 70° C., and the solvent is water.

In another embodiment of this invention, ethyl 2-(4 hydroxyphenyl)-4-methyl-1,3-thiazole-S-carboxylate (a compound of formula (IV)) is prepared by reacting 4-hydroxybenzene carbothiomide (a compound of formula (I)) with ethyl-2-chloroacetoacetate (a compound of formula (V)) at a temperature of about 0° C. to about 150° C. in a solvent. In a preferred embodiment of this invention, the temperature is 80° C. and the solvent is ethanol.

In a further embodiment of this invention, ethyl 2-(4 hydroxyphenyl)-4-methyl-1,3-thiazole-S-carboxylate (a compound of formula (IV)) is prepared by:
(a) reacting 4-hydroxybenzonitrile (a compound of formula (II)), $H_2S$, and sodium hydroxide (a base and compound of formula (III)) under a pressure of at least 10 psi at a temperature of about 0° C. to about 150° C. in a solvent; and
(b) reacting the product of step (a) and ethyl-2-chloroacetoacetate at a temperature of about 0° C. to about 150° C. in a solvent.

In a preferred embodiment of this invention, in (a) the pressure is 60 psi, the temperature is 70° C., and the solvent is water. And in (b) the temperature is 80° C. and the solvent is ethanol. In one particularly preferred embodiment of this invention, in (a) the pressure is 60 psi, the temperature is 70° C., and the solvent is ethanol. And in (b) the temperature is 80° C. and the solvent is ethanol.

This invention will now be described in connection with other particularly preferred embodiments of Scheme 1, which are not intended to limit its scope. On the contrary, the invention covers all alternatives, modifications, and equivalents that are included within the scope of the claims. Thus, the following examples will illustrate an especially preferred practice of the invention, it being understood that the examples are for the purpose of illustration of certain preferred embodiments and are presented to provide what is believed to be the most useful and readily understood description of its procedures and conceptual aspects.

EXAMPLE 1

4-hydroxybenzene carbothioamide

A mixture of 4-Cyanophenol (50.0 g, 0.42 mol), and NaSH (15.5 g, 0.21 mol) in distilled water (125 mL) was stirred at room temperature for 30 minutes. The mixture was then put under a vacuum, flushed with $H_2S$, and the pressure was brought to 40-50 psi for a period of a few minutes. The mixture was then heated to 70° C. and stirred for 40-45 minutes. The mixture was stirred vigorously at 70° C. under constant pressure of 56 psi for 5 hours and 15 minutes. The $H_2S$ pressure was removed and the reaction was cooled to room temperature. The reaction was neutralized to pH 5-7 with 2 M HCl (66 mL). The product was filtered, and the filter cake washed with distilled water (2×50 mL), and dried under a vacuum at 80-85° C. for 22 hours to provide 62.74 g (97.57%) desired product.

EXAMPLE 2

Ethyl 2-(4-hydroxyphenyl)-4-methyl-1,3-thiazole-5-carboxylate

A mixture of 4-Cyanophenol (23.82 g, 0.2 mol), NaOH (8 g, 0.2 mol), and 200 mL ethanol were mixed in a pressure bottle while heated to 80° C. Hydrogen sulfide gas was then introduced and the pressure increased to 30-60 psi until the thioamidation was determined to be complete by HPLC. Without isolating the thioamide product, HCl was added to the bottle until the pH was below 3.5, the $H_2S$ gas was removed, and the bottle was placed under a vacuum for 20 minutes at 30-40° C. The reaction was then heated to 70° C. and ethyl 2-chloroacetoacetate(1.1 eq.) was added to the reaction solution. The reaction was mixed under reflux for 2-3 hours, treated with enough $H_2O$ to dissolve the NaCl salt in the reaction mixture, cooled to room temperature, treated with enough water to precipitate the product, and the solid was collected by filtration. The precipitate was washed with water and dried at 80° C. with nitrogen bleeding to provide 50.50 g (84.2%) of desired product.

What is claimed is:

1. A process for the preparation of a compound of formula (IV)

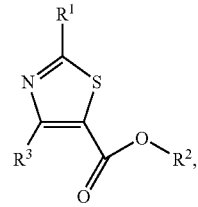

(IV)

wherein
R$^1$ is selected from the group consisting of heteroaryl, phenyl, or phenyl substituted with one, two, three, or four substituents independently selected from the group consisting of $C_1$-$C_6$-alkyl, $C_2$-$C_6$-alkenyl, $C_2$-$C_6$-alkynyl, —OH, —F, —Cl, —Br, —I, —NH$_2$ and —NO$_2$;
R$^2$ is selected from a group consisting of hydrogen, $C_1$-$C_6$-alkyl, $C_2$-$C_6$-alkenyl, and $C_2$-$C_6$-alkynyl; and
R$^3$ is selected from a group consisting of hydrogen, $C_1$-$C_6$-alkyl, $C_2$-$C_6$-alkenyl, and $C_2$-$C_6$-alkynyl;
the process comprising reacting a compound having formula (I)

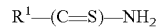

R$^1$—(C=S)—NH$_2$ (I), with a compound having formula (V)

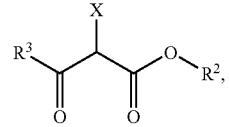

(V)

wherein
X is selected from the group consisting of —Cl, —Br, —I, and —F.

2. The process of claim 1, wherein the process is conducted at a temperature of about 0° C. to about 150° C.

3. The process of claim 1, wherein the process is conducted in a solvent.

4. The process of claim 3, wherein the solvent is ethanol.

5. The process of claim 1, wherein R$^1$ is phenyl substituted with one —OH substituent.

6. The process of claim 1, wherein R$^2$ is ethyl.

7. The process of claim 1, wherein R$^3$ is methyl.

8. The process of claim 1, wherein X is —Cl.

9. The process for the preparation of ethyl 2-(4 hydroxyphenyl)-4-methyl-1,3-thiazole-S-carboxylate, the process comprising reacting 4-hydroxybenzene carbothiomide with ethyl-2-chloroacetoacetate at a temperature of about 0° C. to about 150° C. in an organic solvent.

10. The process of claim 9, wherein the temperature is 80° C. and the organic solvent is ethanol.

11. A process for the preparation of a compound of formula (IV)

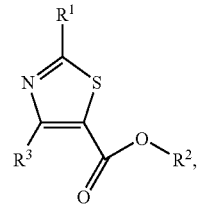

(IV)

$R^1$ is selected from the group consisting of heteroaryl, phenyl, or phenyl substituted with one, two, three, or four substituents independently selected from the group consisting of hydrogen, $C_1$-$C_6$-alkyl, $C_2$-$C_6$-alkenyl, $C_2$-$C_6$-alkynyl, —OH, —F, —Cl, —Br, —I, —$NH_2$;

$R^2$ is selected from the group consisting of hydrogen, $C_1$-$C_6$-alkyl, $C_2$-$C_6$-alkenyl, and $C_2$-$C_6$-alkynyl; and $R^3$ is selected from the group consisting of hydrogen, $C_1$-$C_6$-alkyl, $C_2$-$C_6$-alkenyl, and $C_2$-$C_6$-alkynyl;

the process comprising the steps of:

(a) reacting a compound having formula (II)

$R^1$—C≡N      (II), with a base and $H_2S$ to provide a compound of formula (I)

$R^1$—(C=S)—$NH_2$      (I);

and (b) reacting the product of step (a) with a compound having formula (V)

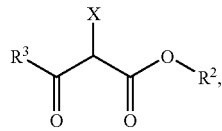

wherein

X is selected from the group comprising —Cl, —Br, —I, and —F.

12. The process of claim 11, wherein the base in step (a) is a compound of formula (III)

$(M)^+(YH)^-$      (III), wherein

M is sodium, potassium, lithium, or —$NH_4$; and

Y is oxygen or sulfur.

13. The process of claim 11, wherein step (a) is conducted under a pressure of at least 10 psi.

14. The process of claim 11, wherein steps (a) and (b) are conducted in solvents.

15. The process of claim 11, wherein steps (a) and (b) are conducted at a temperature of about 0° C. to about 150° C.

16. The process of claim 11, which is conducted as a continuous process.

17. A process for the preparation of ethyl 2-(4 hydroxyphenyl)-4-methyl-1,3-thiazole-S-carboxylate, the process comprising the steps of:

(a) reacting 4-hydroxybenzonitrile, sodium hydroxide, and hydrogen sulfide under a pressure of at least 10 psi at a temperature of about 0° C. to about 150° C. in a solvent; and (b) reacting the product of step (a) and ethyl-2-chloroacetoacetate at a temperature of about 0° C. to about 150° C. in a solvent.

18. The process of claim 17, wherein in (a) the pressure is 60 psi, the temperature is 70° C., and the solvent is water, and in (b) the temperature is 80° C. and the solvent is ethanol.

19. The process of claim 18, wherein the solvent used in (a) is the same solvent used in (b).

20. The process of claim 18, wherein in (a) the pressure is 60 psi, the temperature is 70° C., and the solvent is ethanol, and in (b) the temperature is 80° C. and the solvent is ethanol.

* * * * *

UNITED STATES PATENT AND TRADEMARK OFFICE
CERTIFICATE OF CORRECTION

PATENT NO. : 7,541,475 B2  Page 1 of 1
APPLICATION NO. : 10/903553
DATED : June 2, 2009
INVENTOR(S) : Robbins et al.

It is certified that error appears in the above-identified patent and that said Letters Patent is hereby corrected as shown below:

Column 3, line 50, delete "ethyl acetate" and insert -- ethyl acetate, --.

Column 4, lines 14-16, delete " 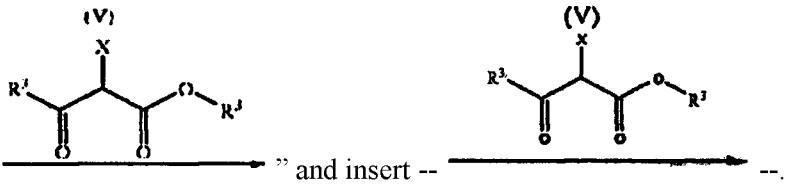 " and insert -- --.

Column 4, line 60, delete "2-(4" and insert -- 2-(4- --.

Column 4, line 63, delete "carbothiomide" and insert -- carbothioamide --.

Column 5, line 1, delete "2-(4" and insert -- 2-(4- --.

Column 6, line 20, in claim 1, delete "a group" and insert -- the group --.

Column 6, line 22, in claim 1, delete "a group" and insert -- the group --.

Column 6, lines 49-50, in claim 9, delete "(4 hydroxyphenyl)" and insert -- (4-hydroxyphenyl) --.

Column 6, line 51, in claim 9, delete "carbothiomide" and insert -- carbothioamide --.

Column 7, line 1, in claim 11, before "$R^1$" insert -- wherein --.

Column 7, line 5, in claim 11, delete "—$NH_2$;" and insert -- —$NH_2$ and —$NO_2$; --.

Column 8, lines 15-16, in claim 17, delete "(4 hydroxyphenyl)" and insert -- (4-hydroxyphenyl) --.

Column 8, line 30, in claim 20, delete "claim 18," and insert -- claim 17, --.

Signed and Sealed this

Eighth Day of June, 2010

David J. Kappos
*Director of the United States Patent and Trademark Office*